United States Patent [19]

Ueki

[11] Patent Number: 5,342,412
[45] Date of Patent: Aug. 30, 1994

[54] DISPOSABLE BODY WARMER

[75] Inventor: Akio Ueki, Osaka, Japan

[73] Assignee: Kiribai Chemical Industry Co., Ltd., Osaka, Japan

[21] Appl. No.: 111,909

[22] Filed: Aug. 26, 1993

Related U.S. Application Data

[63] Continuation-in-part of Ser. No. 793,445, Jan. 7, 1992, abandoned.

[51] Int. Cl.$^5$ .............................................. A61F 7/00
[52] U.S. Cl. .................................... 607/114; 607/96
[58] Field of Search .................. 607/96, 108–112, 607/114

[56] References Cited

U.S. PATENT DOCUMENTS

| | | | |
|---|---|---|---|
| 3,763,622 | 10/1973 | Stanley, Jr. | 607/114 X |
| 3,976,049 | 8/1976 | Yamashita et al. | |
| 4,114,591 | 9/1978 | Nakagawa. | |
| 4,925,743 | 5/1990 | Ikeda et al. | 607/114 X |
| 5,046,479 | 9/1991 | Usui. | |

FOREIGN PATENT DOCUMENTS

| | | | |
|---|---|---|---|
| 58-37075 | 3/1983 | Japan. | |
| 61-276556 | 12/1986 | Japan. | |
| 62-347 | 1/1987 | Japan. | |
| 63-186420 | 11/1988 | Japan. | |
| 63-195829 | 12/1988 | Japan. | |
| 1218447 | 8/1989 | Japan | 607/108 |
| 1-30169 | 9/1989 | Japan. | |
| 1-250252 | 10/1989 | Japan. | |

*Primary Examiner*—Angela D. Sykes
*Attorney, Agent, or Firm*—Armstrong, Westerman, Hattori, McLeland & Naughton

[57] ABSTRACT

A disposable body warmer in which a heat-generating agent which oxidizes and generates heat by the presence of air is contained in a flat bag. At least one surface of the flat bag is made air permeable so that pressure in the flat bag is reduced by exothermic reaction of the heat generating agent, and a self-adhesive layer is provided on either surface of the flat bag. Since the heat-generating agent contains high performance activated carbon having an iodine adsorption of 800 to 1200 mg/g and a methylene blue decoloring power of 100 to 300 mg/g, the rising in temperature is fast in comparison with conventional body warmers.

4 Claims, 2 Drawing Sheets

DISPOSABLE BODY WARMER

CROSS-REFERENCE TO RELATED APPLICATION

This is a continuation-in-part of application Ser. No. 793,445 filed on Jan. 7, 1992 now abandoned.

BACKGROUND OF THE INVENTION

The present invention relates to a disposable body warmer, and, more particularly, to a disposable body warmer which has a good rising characteristic (i.e. the rising in temperature is fast), can maintain the temperature a suitable duration, can avoid bulging of a bag and agglomeration of the heat-generating agent after the beginning of use, i.e. during use, and can use a permeable inner bag having a low water vapor permeability.

A disposable body warmer comprises an air-permeable bag, and a mixture contained in the bag and comprising metal powder such as iron powder available at a relatively low cost and assistants such as water, wood flour and sodium chloride. The disposable body warmer utilizes an exothermic reaction caused by supplying oxygen thereto, and is easy to carry and can be easily used by merely opening an outer bag, so that it occupies a major proportion of body warmers in these days.

Further, in order to make the application of the above-mentioned disposable body warmer to the human body easy and simple, there is proposed a disposable body warmer in which an intransferable self-adhesive layer functioning as a conventional attaching means such as an attaching band and a pocket is employed (refer to, for example, Japanese Examined Utility Model Publication No. 34735/1981).

However, when the disposable body warmer of the adhesion type described above is applied to the human body, there are problems that distribution of contents in a bag becomes uneven (such uneven distribution is particularly significant when the body warmer is applied to the human body in a perpendicular or inclined state), and heat generation is completed at an early stage in one part of the heat-generating agent so that heat distribution of the body warmer becomes uneven. There are further problems that partial extreme increase in thickness of a bag, agglomerated heat-generating agent and the like deteriorates the touch and gives unpleasantness (gives inferior feeling in use) to a user.

In order to solve the problems mentioned above, there is proposed a disposable body warmer in which air permeability of one surface of an inner bag containing the heat-generating agent is controlled to reduce the pressure in the bag (refer to, for example, Japanese Examined Utility Model Publication No. 30169/1989 or Japanese Unexamined Patent Publication No. 149272/1990).

The above-mentioned disposable body warmer, however, has problems that (1) there is scatter in performance of the body warmer because air permeability of the inner bag is evaluated based on air permeability per unit time (Japanese Industrial Standard P 8117 hereinafter, Japanese Industrial Standard being abbreviated as JIS), not water vapor permeability (JIS Z 0280) having a high accuracy, (2) usable inner bags are limited to those having air permeability of 5000 to 10000 sec/100 cc, (3) assistants for preventing agglomeration are not employed in the contents, so that agglomeration of the heat-generating agent cannot be avoided unless not less than 9% by weight of water-holding material is added to the heat-generating agent, and (4) the rise-time is long.

It is an object of the present invention to provide a disposable body warmer capable of solving the above-mentioned drawbacks. That is, an object of the present invention is to provide a disposable body warmer which requires a short time to raise its temperature up to a predetermined temperature just from the beginning of heat generation, has a suitable duration for various kinds of uses and is free from bulging and agglomeration of the heat-generating agent after the beginning of use thereof.

SUMMARY OF THE INVENTION

In accordance with the present invention, there is provided a disposable body warmer comprising a heat-generating agent which oxidizes and generates heat in the presence of air, a flat bag containing the heat-generating agent and an airtight bag containing the flat bag, wherein at least one surface of the flat bag is made air permeable so that pressure in the flat bag is reduced by exothermic reaction of the heat-generating agent, a self-adhesive layer is provided on either surface of the flat bag, and the heat-generating agent contains high performance activated carbon having an iodine adsorption of 800 to 1200 mg/g and a methylene blue decoloring power of 100 to 300 mg/g.

Water vapor permeability of the air permeable surface of the flat bag is preferably from 340 to 1000 g/m$^2$·24 h, and more preferably from 350 to 700 g/m$^2$·24 h.

Further, the heat-generating agent preferably contains 2 to 6% by weight of silica gel and/or alumina.

DETAILED DESCRIPTION

A disposable body warmer of the present invention is explained in detail hereinafter.

Figure 1:
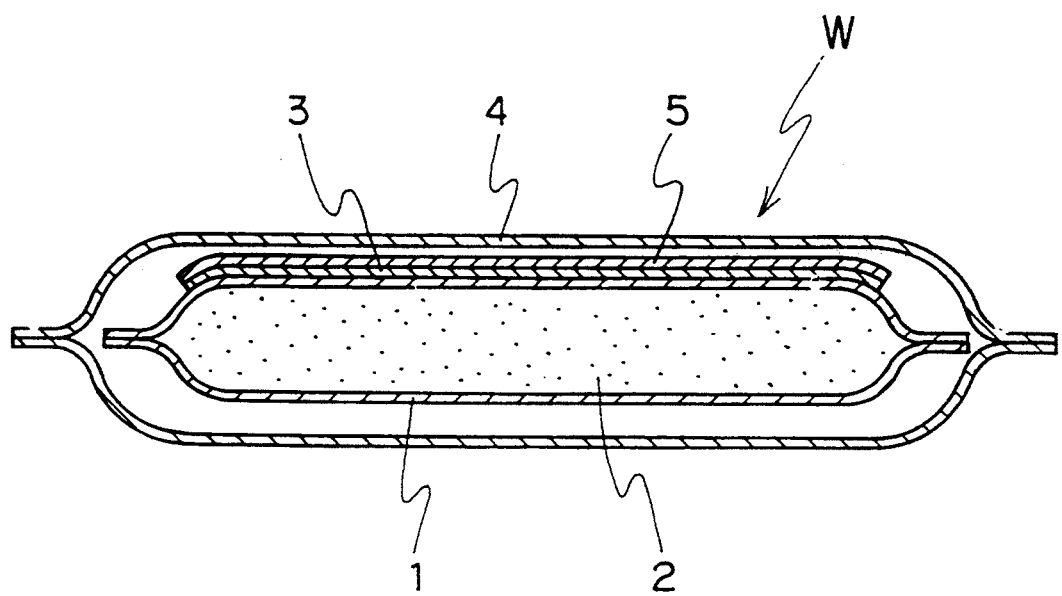
FIG. 1 is a sectional explanatory view of an embodiment of a disposable body warmer of the present invention.
Figure 2:
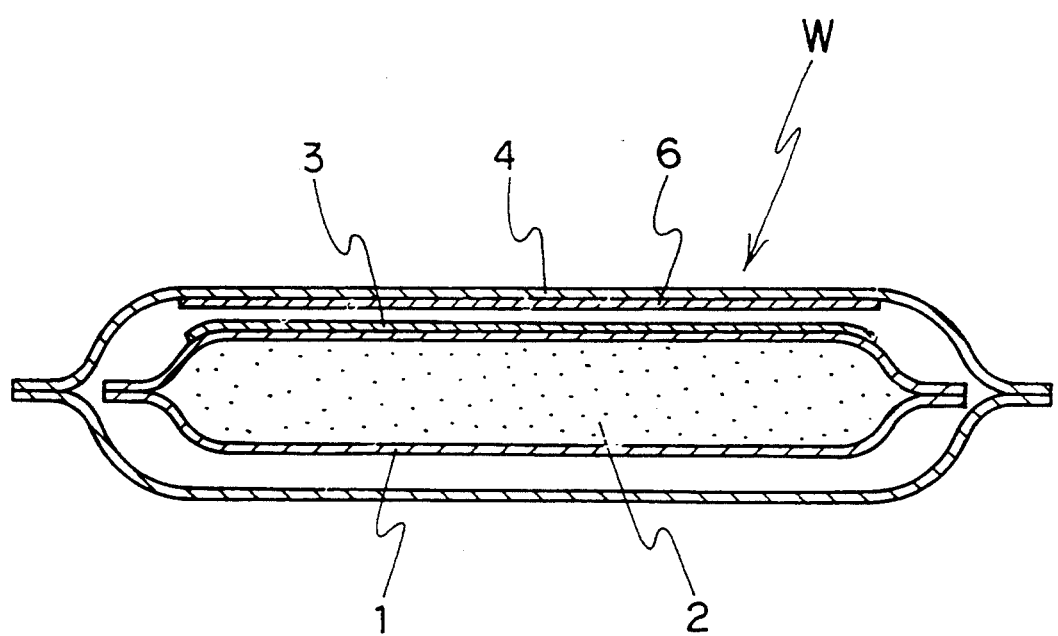
FIG. 2 a sectional explanatory view of another embodiment of a disposable body warmer of the present invention.

In FIGS. 1 to 2, symbol W is an embodiment of a disposable body warmer of the present invention. The body warmer W is composed of a flat inner bag 1, heat-generating agent 2 contained in the inner bag 1, a self-adhesive layer formed on one surface of the inner bag 1, and an airtight outer bag 4 containing the inner bag 1.

One surface of the flat bag 1 is air permeable while the other surface thereof is air impermeable. In the embodiment shown in FIGS. 1 to 2, the under surface of the inner bag 1 is made air permeable. In producing the inner bag 1, both surfaces thereof might be made of air permeable material and one surface might be made air impermeable or air adjustable by forming a self-adhesive layer 3 entirely or partially on one surface. There might also be employed an inner bag in which one surface thereof is made air permeable while the other surface thereof is made air impermeable and a self-adhesive layer is formed on the air impermeable surface entirely or partially. In short, at least one surface of the inner bag is air permeable, and a self-adhesive layer is formed on either surface entirely or partially.

With respect to air permeability of the inner bag 1, it is possible to select a material for the inner bag 1 based on air permeability per unit time (sec/100 ml: time (sec) required for a given amount of air (100 ml) to pass through an unit area (645 mm$^2$) under pressure, JIS P 8117). Evaluation based on air permeability per unit time, however, has drawbacks that there is a large scatter in the results due to features of test method employing forced air passage, resulting in an inferior accuracy, and it requires expensive analysis cost and a long test time period. Accordingly, it is preferable, instead of air permeability per unit time, to employ water vapor permeability (g/m$^2$·24 h: An amount of water vapor passing through a film of an unit area in a given period of time). According to condition B in JIS Z 0208, a vapor-proof package material is used as a boundary surface. The relative humidity of air on one side is kept 90% while air on the other side is kept dry by moisture-absorbing agent at 40° C. The mass (g) of water vapor passing through the boundary surface in 24 hours is converted into the mass per 1 m$^2$. Preferably the water vapor permeability is from 340 to 1000 g/m$^2$·24h, and more preferably the water vapor permeability is from 350 to 700 g/m$^2$·24 h. Though the other factors have influence, in general, when the water vapor permeability is less than 340 g/m$^2$·24 h, there are disadvantages that sufficient exothermic reaction cannot be obtained, i.e. the temperature of the body warmers is not raised. On the other hand, when the water vapor permeability is more than 1000 g/m$^2$·24 h, there are disadvantages that the body warmers become too hot, the duration is too short, and the body warmers inflate during or after use.

Though materials for the inner bag 1 are not limited in the present invention, it is preferable to use such materials that have good fitness to the human body, underwears and the like, stable quality, applicability for heat sealing, and are soft and strong, and not nappy. Usable concrete examples are, for example, plastic-like or rubber-like flexible thermoplastic sheets or films comprising polyurethane, polypropylene or polyethylene, or modifications thereof; and a single layer or complex layer of non-woven fabric, polyvinyl chloride, polyester or polystyrene. As a method for controlling the air permeability of an air permeable surface of an inner bag 1, there is a method wherein an appropriate heat welding treatment is applied to a sheet or film on which minute continuous holes are formed. Concretely speaking, the air permeability can be controlled, for example, by uniformly distributing or entirely applying a heat welding agent which is heated appropriately on a sheet or film having uniform continuous holes of 1 to 50 μm in diameter.

The air permeability can be also controlled by laminating a resin film, on which minute air permeable holes are formed, to a non woven fabric.

Though the size of the inner bag 1 is not particularly limited in the present invention, inner bags of a size from 4×6 cm to 15×20 cm can be usually employed.

Numeral 2 is a heat-generating agent comprising iron powder, activated carbon, water, a water-holding material (wood flour, vermiculite, diatomaceous earth, pearlite, silica gel, alumina, water-absorbing resin and the like), and sodium chloride. In the present specification, the term "heat-generating agent" means all compositions contained in the body warmer. With respect to the iron powder, water-holding material, sodium chloride and the like, those which are used in the usual disposable body warmers can be used. The proportions thereof is not limited in the present invention, and accordingly usual proportions might be employed. Concretely speaking, 47 to 70% (% by weight, hereinafter the same) of iron powder, 15 to 35% of water, 3 to 9% of water-holding material, 5 to 12% of activated carbon, 0.5 to 4% of sodium chloride and the like are used. They are so adjusted as to have maximum exothermic reaction temperature by oxidation thereof of, preferably, 53° to 57° C.

One of the features of the present invention is the use of, as the above-mentioned activated carbon, high performance activated carbon having specific properties. That is, in the disposable body warmer of the present invention, high performance activated carbon having an iodine adsorption of 800 to 1200 mg/g and a methylene blue decoloring power of 100 to 300 mg/g is used. The iodine adsorption is determined, as prescribed in JIS K 1474, as follows. That is, an iodine solution is added to samples and a supernatant liquid is separated after adsorption is carried out. Then, a starch solution as an indicator is added to the separated supernatant liquid to titrate with a sodium thiosulfate solution. The iodine adsorption is determined by the concentration of the remaining iodine. The methylene blue decoloring powder is determined, as prescribed in JIS K 1470, as follows. That is, methylene blue solution A is added to samples and filtration is carried out after shaking by a shaker. The chromaticity of the filtrate is compared with that of methylene blue solution B, and the methylene blue decoloring power is determined by the amount of added methylene blue solution A required for making the chromaticity of filtrate coincide with that of methylene blue solution B. Both factors relate to adsorption performance of activated carbon. By using activated carbon having a specific range of adsorption performance, it becomes possible to shorten the time required for raising temperature of disposable body warmers up to a predetermined temperature just from the beginning of heat generation, and to maintain a suitable duration. That is, the duration required of body warmers which is typically within 20 hours varies depending on use of the body warmers. In general, a duration of 5 to 6 hours is necessary for outdoor leisure such as fishing, skating, skiing and sports watching, while a duration of 12 to 13 hours is necessary for outdoor work or business such as sailing, window cleaning, construction work and road building. Further, duration of 17 to 18 hours is necessary for indoor use (personal warming). A body warmer should not be used during sleeping in order to avoid low temperature burn.

Moreover, by using activated carbon of high quality, there can be used inner bags of wider range of water vapor permeability. In manufacturing inner bags, it is difficult to control the water vapor permeability thereof to a predetermined value. In general, water vapor permeability vary widely by about ±30% from a predetermined value. When using conventional activated carbon, about 25% of inner bags cannot be used. However, when using activated carbon of high quality, it is possible to compensate the scattering in water vapor permeability of inner bags manufactured, i.e., to use most of inner bags (about 90% of inner bags) manufactured.

Further, by adding 2 to 6% of silica gel and/or alumina to the above-mentioned heat-generating agent 2, the bulging of the inner bag and agglomeration of the heat-generating agent after the beginning of use mentioned above can be effectively prevented.

When the proportion of silica gel and/or alumina is less than 2%, the heat-generating agent agglomerates after the beginning of use. On the other hand, when the proportion is more than 6%, the amounts of other components such as iron powder, water-holding agent, activated carbon, sodium chloride and the like are not suitable, so that the heat-generating agent becomes bulky and the effects of the other components are lessened. That is, the time required for raising temperature of the heat-generating agent up to a predetermined temperature just after the beginning of heat generation is lengthened and duration is shortened.

Numeral 3 is a self-adhesive layer comprising usual self-adhesive materials including rubber and the like as a main material. The self-adhesive layer 3 is provided on one surface of the inner bag 1. The self-adhesive layer 3 might be provided entirely on one surface of the inner bag 1, or might be provided partially so as to form suitable patterns such as a fringe pattern, grid pattern and polka dots. The self-adhesive layer 3 is formed after the above-mentioned heat-generating agent 2 is charged into the inner bag 1.

In the embodiment shown in FIG. 1, a release paper 5 covers the surface of the self-adhesive layer 3. In use, the release paper 5 is peeled off, and the inner bag 1 is adhered to a desired portion using the self-adhesive layer 3.

Numeral 4 is an airtight outer bag comprising a holeless film made of polyethylene, polypropylene and the like. In the embodiment shown in FIG. 2, the release layer 6 is formed on the inner surface of the outer bag, whereby covering and protecting the self-adhesive layer 3 formed on the inner bag. In this case, the outer bag 4 functions also as a release paper in the conventional body warmer, so that the inner bag 1 can be fixed to a desired portion by merely opening the outer bag 4.

Next, the disposable body warmer of the present invention is explained based on Examples. The present invention is not, however, limited thereto.

The experiments were carried out by suitably varying iodine adsorption (mg/g) of activated carbon, while maintaining water vapor permeability constant. Measurement was performed on the basis of JIS S 4100, and the rise-time (minutes) and duration (hours) were examined. Further, the content ratio (%: ratio to heat-generating agent) of silica gel was varied to 0, 0.5, 1, 1.5, 2, 2.5, 3, 3.5 or 4. The state of agglomeration of the heat-generating agent after use was judged in three stages (agglomerated, more or less agglomerated, not agglomerated).

The number of samples tested was 10, and the maximum temperature, rise-time and duration were obtained as follows.

Maximum Temperature

Figure 3:
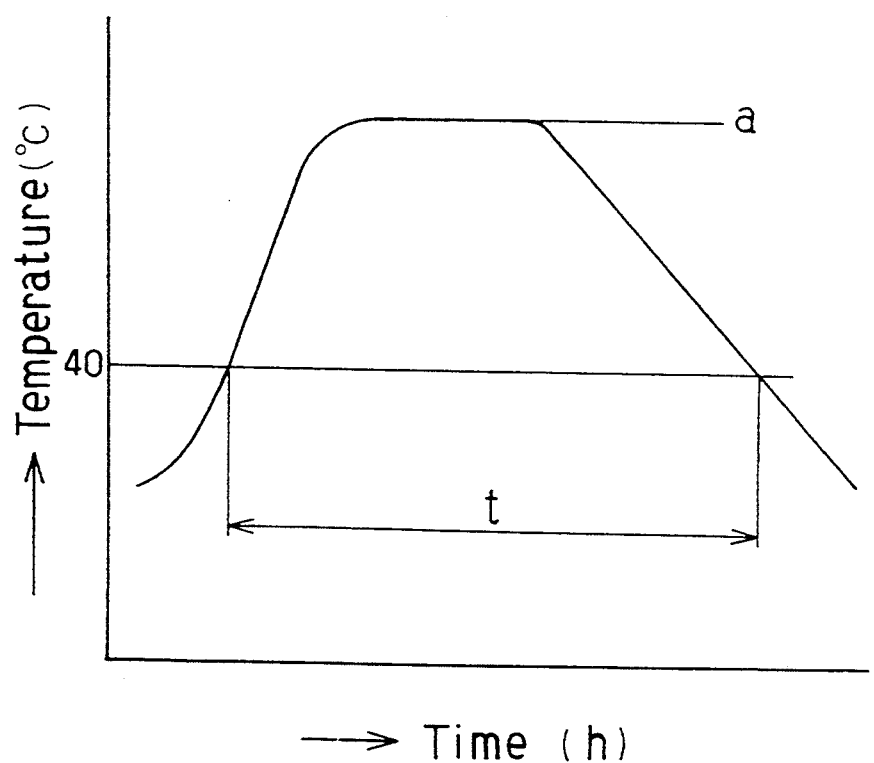
FIG. 3 is a view showing a pattern of temperature change of a disposable body warmer.

Average of measured maximum temperatures of all samples. Refer to a in FIG. 3.

Rise-time

Average of measured times of eight samples required for raising the temperature of the samples up to 40° C. from the beginning of heat generation, wherein the maximum value and minimum value are excluded (provided that only one value of plural maximum values or minimum values is excluded when there are plural maximum values or minimum values).

Duration

Average of measured durations of eight samples from the beginning of heat generation to the passage of maximum temperature, wherein the maximum value and minimum value are excluded (provided that only one value of plural maximum values or minimum values is excluded when there are plural maximum values or minimum values, and that a fraction less than one hour is omitted). Refer to t in FIG. 3.

EXAMPLES 1 to 17 and COMPARATIVE EXAMPLES 1 to 5

(Water Vapor Permeability: 210 g/m$^2$·24 h)

There were prepared inner bags (length: 130 mm, width: 95 mm, sealed width: 6 mm) wherein a lamination of porous polyethylene and nylon non-woven fabric which was heat welded to control air permeability was used as an air permeable surface, and polyethylene having thereon an acrylic self-adhesive layer was used as an air impermeable surface. 36 g of heat-generating agent obtained by mixing 56 parts of reduced iron powder MR-2 (iron powder produced by Dowa Teppun Kogyo Kabushiki Kaisha), 27 parts of 10% brine, 9 parts of high performance activated carbon, 3 parts of Hirukon S-1 (vermiculite produced by Hiruishi Kagaku Kogyo Kabushiki Kaisha), 2 parts of KI Gel-201K (water-absorbing resin produced by Kuraray Co., Ltd.) and 3 parts of Silica Gel HA40 (silica gel produced by Fuji Shirishia Kagaku Kabushiki Kaisha) was charged into each inner bag. The heat generation performance of thus prepared warmers was measured according to JIS S 4100 as mentioned above. The results are summarized in Table 1.

TABLE 1

| No. | Iodine adsorption (mg/g) | Methylene blue decoloring power (mg/g) | Maximum Temp. (°C.) | Rise-time (min.) | Duration (hour) |
| --- | --- | --- | --- | --- | --- |
| Ex. 1 | 880 | 100 | 32 | * | * |
| Ex. 2 | 880 | 200 | 33 | * | * |
| Ex. 3 | 910 | 100 | 33 | * | * |
| Ex. 4 | 910 | 140 | 33 | * | * |
| Ex. 5 | 910 | 160 | 35 | * | * |
| Ex. 6 | 910 | 200 | 35 | * | * |
| Ex. 7 | 910 | 300 | 35 | * | * |
| Ex. 8 | 1000 | 100 | 35 | * | * |
| Ex. 9 | 1000 | 140 | 35 | * | * |
| Ex. 10 | 1000 | 160 | 36 | * | * |
| Ex. 11 | 1000 | 200 | 40 | 19 | 27 |
| Ex. 12 | 1000 | 300 | 40 | 19 | 27 |
| Ex. 13 | 1200 | 100 | 40 | 19 | 27 |
| Ex. 14 | 1200 | 140 | 40 | 19 | 27 |
| Ex. 15 | 1200 | 160 | 41 | 19 | 27 |
| Ex. 16 | 1200 | 200 | 41 | 19 | 27 |
| Ex. 17 | 1200 | 300 | 41 | 19 | 27 |
| Com. Ex. 1 | 500 | 100 | 30 | * | * |
| Com. Ex. 2 | 500 | 200 | 30 | * | * |
| Com. Ex. 3 | 700 | 100 | 31 | * | * |
| Com. Ex. 4 | 700 | 200 | 32 | * | * |
| Com. Ex. 5 | 910 | 80 | 31 | * | * |

Note:
Symbol * means that measurement based on JIS was impossible.

EXAMPLE 18 to 34 and COMPARATIVE EXAMPLES 6 to 10

(Water Vapor Permeability: 340 g/m$^2$·24 h)

Body warmers were prepared and predetermined measurements were carried out in the same manner as Example 1 except that water vapor permeability of air permeable surfaces of inner bags was changed to 340 g/m²·24 h. The results are summarized in Table 2.

TABLE 2

| No. | Iodine adsorption (mg/g) | Methylene blue decoloring power (mg/g) | Maximum Temp. (°C.) | Rise-time (min.) | Duration (hour) |
|---|---|---|---|---|---|
| Ex. 18 | 880 | 100 | 35 | * | * |
| Ex. 19 | 880 | 200 | 36 | * | * |
| Ex. 20 | 910 | 100 | 36 | * | * |
| Ex. 21 | 910 | 140 | 38 | * | * |
| Ex. 22 | 910 | 160 | 38 | * | * |
| Ex. 23 | 910 | 200 | 38 | * | * |
| Ex. 24 | 910 | 300 | 39 | * | * |
| Ex. 25 | 1000 | 100 | 40 | 18 | 25 |
| Ex. 26 | 1000 | 140 | 40 | 18 | 25 |
| Ex. 27 | 1000 | 160 | 42 | 18 | 25 |
| Ex. 28 | 1000 | 200 | 43 | 18 | 25 |
| Ex. 29 | 1000 | 300 | 43 | 18 | 25 |
| Ex. 30 | 1200 | 100 | 43 | 17 | 25 |
| Ex. 31 | 1200 | 140 | 43 | 17 | 25 |
| Ex. 32 | 1200 | 160 | 43 | 17 | 25 |
| Ex. 33 | 1200 | 200 | 43 | 17 | 25 |
| Ex. 34 | 1200 | 300 | 43 | 17 | 25 |
| Com. Ex. 6 | 500 | 100 | 32 | * | * |
| Com. Ex. 7 | 500 | 200 | 32 | * | * |
| Com. Ex. 8 | 700 | 100 | 33 | * | * |
| Com. Ex. 9 | 700 | 200 | 34 | * | * |
| Com. Ex. 10 | 910 | 80 | 33 | * | * |

Note:
Symbol * means that measurement based on JIS was impossible.

EXAMPLE 35 to 51 and COMPARATIVE EXAMPLES 11 to 15

(Water Vapor Permeability: 360 g/m²·24 h)

Body warmers were prepared and predetermined measurements were carried out in the same manner as Example 1 except that water vapor permeability of air permeable surfaces of inner bags was changed to 360 g/m²·24 h. The results are summarized in Table 3.

TABLE 3

| No. | Iodine adsorption (mg/g) | Methylene blue decoloring power (mg/g) | Maximum Temp. (°C.) | Rise-time (min.) | Duration (hour) |
|---|---|---|---|---|---|
| Ex. 35 | 880 | 100 | 38 | * | * |
| Ex. 36 | 880 | 200 | 39 | * | * |
| Ex. 37 | 910 | 100 | 40 | 17 | 25 |
| Ex. 38 | 910 | 140 | 40 | 17 | 25 |
| Ex. 39 | 910 | 160 | 41 | 17 | 25 |
| Ex. 40 | 910 | 200 | 41 | 17 | 24 |
| Ex. 41 | 910 | 300 | 41 | 17 | 24 |
| Ex. 42 | 1000 | 100 | 43 | 17 | 24 |
| Ex. 43 | 1000 | 140 | 44 | 16 | 24 |
| Ex. 44 | 1000 | 160 | 45 | 16 | 24 |
| Ex. 45 | 1000 | 200 | 45 | 16 | 24 |
| Ex. 46 | 1000 | 300 | 45 | 16 | 24 |
| Ex. 47 | 1200 | 100 | 45 | 15 | 24 |
| Ex. 48 | 1200 | 140 | 45 | 15 | 24 |
| Ex. 49 | 1200 | 160 | 45 | 15 | 24 |
| Ex. 50 | 1200 | 200 | 45 | 15 | 24 |
| Ex. 51 | 1200 | 300 | 45 | 15 | 24 |
| Com. Ex. 11 | 500 | 100 | 32 | * | * |
| Com. Ex. 12 | 500 | 200 | 33 | * | * |
| Com. Ex. 13 | 700 | 100 | 35 | * | * |
| Com. Ex. 14 | 700 | 200 | 36 | * | * |
| Com. Ex. 15 | 910 | 80 | 35 | * | * |

Note:
Symbol * means that measurement based on JIS was impossible.

EXAMPLE 52 to 68 and COMPARATIVE EXAMPLES 16 to 20

(Water Vapor Permeability: 400 g/m²·24 h)

Body warmers were prepared and predetermined measurements were carried out in the same manner as Example 1 except that water vapor permeability of air permeable surfaces of inner bags was changed to 400 g/m²·24 h. The results are summarized in Table 4.

TABLE 4

| No. | Iodine adsorption (mg/g) | Methylene blue decoloring power (mg/g) | Maximum Temp. (°C.) | Rise-time (min.) | Duration (hour) |
|---|---|---|---|---|---|
| Ex. 52 | 880 | 100 | 50 | 15 | 20 |
| Ex. 53 | 880 | 200 | 51 | 15 | 19 |
| Ex. 54 | 910 | 100 | 51 | 15 | 19 |
| Ex. 55 | 910 | 140 | 51 | 15 | 19 |
| Ex. 56 | 910 | 160 | 52 | 14 | 18 |
| Ex. 57 | 910 | 200 | 52 | 14 | 18 |
| Ex. 58 | 910 | 300 | 52 | 14 | 18 |
| Ex. 59 | 1000 | 100 | 52 | 13 | 18 |
| Ex. 60 | 1000 | 140 | 52 | 13 | 18 |
| Ex. 61 | 1000 | 160 | 53 | 13 | 17 |
| Ex. 62 | 1000 | 200 | 53 | 13 | 17 |
| Ex. 63 | 1000 | 300 | 53 | 13 | 17 |
| Ex. 64 | 1200 | 100 | 54 | 12 | 17 |
| Ex. 65 | 1200 | 140 | 54 | 12 | 17 |
| Ex. 66 | 1200 | 160 | 54 | 12 | 17 |
| Ex. 67 | 1200 | 200 | 54 | 12 | 17 |
| Ex. 68 | 1200 | 300 | 54 | 12 | 17 |
| Com. Ex. 16 | 500 | 100 | 45 | 20 | 26 |
| Com. Ex. 17 | 500 | 200 | 46 | 19 | 26 |
| Com. Ex. 18 | 700 | 100 | 47 | 19 | 24 |
| Com. Ex. 19 | 700 | 200 | 48 | 19 | 24 |
| Com. Ex. 20 | 910 | 80 | 47 | 19 | 24 |

EXAMPLE 69 to 85 and COMPARATIVE EXAMPLES 21 to 25

(Water Vapor Permeability: 450 g/m²·24 h)

Body warmers were prepared and predetermined measurements were carried out in the same manner as Example 1 except that water vapor permeability of air permeable surfaces of inner bags was changed to 450 g/m²·24 h. The results are summarized in Table 5.

TABLE 5

| No. | Iodine adsorption (mg/g) | Methylene blue decoloring power (mg/g) | Maximum Temp. (°C.) | Rise-time (min.) | Duration (hour) |
|---|---|---|---|---|---|
| Ex. 69 | 880 | 100 | 50 | 15 | 20 |
| Ex. 70 | 880 | 200 | 51 | 14 | 19 |
| Ex. 71 | 910 | 100 | 51 | 13 | 19 |
| Ex. 72 | 910 | 140 | 52 | 13 | 18 |
| Ex. 73 | 910 | 160 | 52 | 13 | 18 |
| Ex. 74 | 910 | 200 | 52 | 13 | 18 |
| Ex. 75 | 910 | 300 | 53 | 12 | 17 |
| Ex. 76 | 1000 | 100 | 53 | 12 | 17 |
| Ex. 77 | 1000 | 140 | 53 | 12 | 17 |
| Ex. 78 | 1000 | 160 | 53 | 12 | 17 |
| Ex. 79 | 1000 | 200 | 54 | 12 | 17 |
| Ex. 80 | 1000 | 300 | 55 | 12 | 16 |
| Ex. 81 | 1200 | 100 | 55 | 11 | 16 |
| Ex. 82 | 1200 | 140 | 55 | 11 | 16 |
| Ex. 83 | 1200 | 160 | 55 | 11 | 16 |
| Ex. 84 | 1200 | 200 | 55 | 11 | 16 |
| Ex. 85 | 1200 | 300 | 55 | 11 | 16 |
| Com. Ex. 21 | 500 | 100 | 47 | 19 | 24 |
| Com. Ex. 22 | 500 | 200 | 48 | 19 | 24 |
| Com. Ex. 23 | 700 | 100 | 49 | 17 | 23 |
| Com. Ex. 24 | 700 | 200 | 50 | 17 | 22 |

TABLE 5-continued

| No. | Iodine adsorption (mg/g) | Methylene blue decoloring power (mg/g) | Maximum Temp. (°C) | Rise-time (min.) | Duration (hour) |
|---|---|---|---|---|---|
| Com. Ex. 25 | 910 | 80 | 49 | 17 | 23 |

EXAMPLE 86 to 102 and COMPARATIVE EXAMPLES 26 to 30

(Water Vapor Permeability: 500 g/m$^2$·24 h)

Body warmers were prepared and predetermined measurements were carried out in the same manner as Example 1 except that water vapor permeability of air permeable surfaces of inner bags was changed to 500 g/m$^2$·24 h. The results are summarized in Table 6.

TABLE 6

| No. | Iodine adsorption (mg/g) | Methylene blue decoloring power (mg/g) | Maximum Temp. (°C) | Rise-time (min.) | Duration (hour) |
|---|---|---|---|---|---|
| Ex. 86 | 880 | 100 | 52 | 12 | 17 |
| Ex. 87 | 880 | 200 | 52 | 12 | 17 |
| Ex. 88 | 910 | 100 | 52 | 10 | 17 |
| Ex. 89 | 910 | 140 | 53 | 10 | 17 |
| Ex. 90 | 910 | 160 | 54 | 10 | 17 |
| Ex. 91 | 910 | 200 | 54 | 10 | 17 |
| Ex. 92 | 910 | 300 | 54 | 10 | 16 |
| Ex. 93 | 1000 | 100 | 54 | 9 | 16 |
| Ex. 94 | 1000 | 140 | 54 | 9 | 16 |
| Ex. 95 | 1000 | 160 | 54 | 9 | 16 |
| Ex. 96 | 1000 | 200 | 55 | 9 | 16 |
| Ex. 97 | 1000 | 300 | 55 | 9 | 15 |
| Ex. 98 | 1200 | 100 | 55 | 8 | 15 |
| Ex. 99 | 1200 | 140 | 55 | 8 | 15 |
| Ex. 100 | 1200 | 160 | 56 | 8 | 16 |
| Ex. 101 | 1200 | 200 | 56 | 8 | 15 |
| Ex. 102 | 1200 | 300 | 56 | 8 | 15 |
| Com. Ex. 26 | 500 | 100 | 48 | 19 | 22 |
| Com. Ex. 27 | 500 | 200 | 40 | 18 | 22 |
| Com. Ex. 28 | 700 | 100 | 51 | 14 | 19 |
| Com. Ex. 29 | 700 | 200 | 52 | 14 | 19 |
| Com. Ex. 30 | 910 | 80 | 51 | 14 | 19 |

EXAMPLE 103 to 119 and COMPARATIVE EXAMPLES 31 to 35

(Water Vapor Permeability: 550 g/m$^2$·24 h)

Body warmers were prepared and predetermined measurements were carried out in the same manner as Example 1 except that water vapor permeability of air permeable surfaces of inner bags was changed to 550 g/m$^2$·24 h. The results are summarized in Table 7.

TABLE 7

| No. | Iodine adsorption (mg/g) | Methylene blue decoloring power (mg/g) | Maximum Temp. (°C) | Rise-time (min.) | Duration (hour) |
|---|---|---|---|---|---|
| Ex. 103 | 880 | 100 | 52 | 11 | 16 |
| Ex. 104 | 880 | 200 | 52 | 11 | 16 |
| Ex. 105 | 910 | 100 | 52 | 10 | 15 |
| Ex. 106 | 910 | 140 | 52 | 10 | 15 |
| Ex. 107 | 910 | 160 | 53 | 10 | 15 |
| Ex. 108 | 910 | 200 | 53 | 10 | 15 |
| Ex. 109 | 910 | 300 | 53 | 10 | 14 |
| Ex. 110 | 1000 | 100 | 54 | 9 | 14 |
| Ex. 111 | 1000 | 140 | 54 | 9 | 14 |
| Ex. 112 | 1000 | 160 | 55 | 9 | 14 |
| Ex. 113 | 1000 | 200 | 55 | 9 | 14 |
| Ex. 114 | 1000 | 300 | 55 | 9 | 13 |
| Ex. 115 | 1200 | 100 | 55 | 8 | 14 |
| Ex. 116 | 1200 | 140 | 56 | 8 | 13 |
| Ex. 117 | 1200 | 160 | 56 | 8 | 13 |
| Ex. 118 | 1200 | 200 | 56 | 8 | 13 |
| Ex. 119 | 1200 | 300 | 56 | 8 | 13 |
| Com. Ex. 31 | 500 | 100 | 48 | 16 | 20 |
| Com. Ex. 32 | 500 | 200 | 49 | 16 | 20 |
| Com. Ex. 33 | 700 | 100 | 51 | 16 | 18 |
| Com. Ex. 34 | 700 | 200 | 52 | 14 | 18 |
| Com. Ex. 35 | 910 | 80 | 51 | 16 | 18 |

EXAMPLE 120 to 136 and COMPARATIVE EXAMPLES 36 to 40

(Water Vapor Permeability: 600 g/m$^2$·24 h)

Body warmers were prepared and predetermined measurements were carried out in the same manner as Example 1 except that water vapor permeability of air permeable surfaces of inner bags was changed to 600 g/m$^2$·24 h. The results are summarized in Table 8.

TABLE 8

| No. | Iodine adsorption (mg/g) | Methylene blue decoloring power (mg/g) | Maximum Temp. (°C) | Rise-time (min.) | Duration (hour) |
|---|---|---|---|---|---|
| Ex. 120 | 880 | 100 | 54 | 8 | 16 |
| Ex. 121 | 880 | 200 | 54 | 8 | 16 |
| Ex. 122 | 910 | 100 | 54 | 8 | 16 |
| Ex. 123 | 910 | 140 | 54 | 8 | 16 |
| Ex. 124 | 910 | 160 | 55 | 8 | 15 |
| Ex. 125 | 910 | 200 | 55 | 8 | 15 |
| Ex. 126 | 910 | 300 | 56 | 8 | 15 |
| Ex. 127 | 1000 | 100 | 56 | 7 | 14 |
| Ex. 128 | 1000 | 140 | 56 | 7 | 14 |
| Ex. 129 | 1000 | 160 | 57 | 7 | 13 |
| Ex. 130 | 1000 | 200 | 58 | 7 | 13 |
| Ex. 131 | 1000 | 300 | 58 | 7 | 13 |
| Ex. 132 | 1200 | 100 | 58 | 6 | 13 |
| Ex. 133 | 1200 | 140 | 58 | 6 | 13 |
| Ex. 134 | 1200 | 160 | 59 | 6 | 12 |
| Ex. 135 | 1200 | 200 | 59 | 6 | 12 |
| Ex. 136 | 1200 | 300 | 59 | 6 | 12 |
| Com. Ex. 36 | 500 | 100 | 49 | 14 | 19 |
| Com. Ex. 37 | 500 | 200 | 50 | 13 | 19 |
| Com. Ex. 38 | 700 | 100 | 51 | 10 | 17 |
| Com. Ex. 39 | 700 | 200 | 52 | 10 | 17 |
| Com. Ex. 40 | 910 | 80 | 51 | 10 | 17 |

EXAMPLE 137 to 153 and COMPARATIVE EXAMPLES 41 to 45

(Water Vapor Permeability: 650 g/m$^2$·24 h)

Body warmers were prepared and predetermined measurements were carried out in the same manner as Example 1 except that water vapor permeability of air permeable surfaces of inner bags was changed to 650 g/m$^2$·24 h. The results are summarized in Table 9.

TABLE 9

| No. | Iodine adsorption (mg/g) | Methylene blue decoloring power (mg/g) | Maximum Temp. (°C) | Rise-time (min.) | Duration (hour) |
|---|---|---|---|---|---|
| Ex. 137 | 880 | 100 | 55 | 8 | 14 |

TABLE 9-continued

| No. | Iodine adsorption (mg/g) | Methylene blue decoloring power (mg/g) | Maximum Temp. (°C.) | Rise-time (min.) | Duration (hour) |
|---|---|---|---|---|---|
| Ex. 138 | 880 | 200 | 56 | 8 | 14 |
| Ex. 139 | 910 | 100 | 56 | 8 | 14 |
| Ex. 140 | 910 | 140 | 56 | 8 | 14 |
| Ex. 141 | 910 | 160 | 58 | 8 | 12 |
| Ex. 142 | 910 | 200 | 58 | 8 | 12 |
| Ex. 143 | 910 | 300 | 58 | 8 | 12 |
| Ex. 144 | 1000 | 100 | 58 | 7 | 12 |
| Ex. 145 | 1000 | 140 | 58 | 7 | 12 |
| Ex. 146 | 1000 | 160 | 59 | 7 | 11 |
| Ex. 147 | 1000 | 200 | 59 | 7 | 11 |
| Ex. 148 | 1000 | 300 | 59 | 7 | 11 |
| Ex. 149 | 1200 | 100 | 59 | 6 | 11 |
| Ex. 150 | 1200 | 140 | 59 | 6 | 11 |
| Ex. 151 | 1200 | 160 | 60 | 6 | 11 |
| Ex. 152 | 1200 | 200 | 60 | 6 | 11 |
| Ex. 153 | 1200 | 300 | 60 | 6 | 11 |
| Com. Ex. 41 | 500 | 100 | 50 | 12 | 17 |
| Com. Ex. 42 | 500 | 200 | 51 | 12 | 17 |
| Com. Ex. 43 | 700 | 100 | 52 | 9 | 15 |
| Com. Ex. 44 | 700 | 200 | 53 | 9 | 15 |
| Com. Ex. 45 | 910 | 80 | 52 | 9 | 15 |

EXAMPLE 154 to 170 and COMPARATIVE EXAMPLES 46 to 50

(Water Vapor Permeability: 700 g/m$^2$·24 h)

Body warmers were prepared and predetermined measurements were carried out in the same manner as Example 1 except that water vapor permeability of air permeable surfaces of inner bags was changed to 700 g/m$^2$·24 h. The results are summarized in Table 10.

TABLE 10

| No. | Iodine adsorption (mg/g) | Methylene blue decoloring power (mg/g) | Maximum Temp. (°C.) | Rise-time (min.) | Duration (hour) |
|---|---|---|---|---|---|
| Ex. 154 | 880 | 100 | 57 | 7 | 13 |
| Ex. 155 | 880 | 200 | 58 | 7 | 12 |
| Ex. 156 | 910 | 100 | 58 | 7 | 12 |
| Ex. 157 | 910 | 140 | 58 | 7 | 12 |
| Ex. 158 | 910 | 160 | 60 | 6 | 11 |
| Ex. 159 | 910 | 200 | 60 | 6 | 11 |
| Ex. 160 | 910 | 300 | 60 | 6 | 11 |
| Ex. 161 | 1000 | 100 | 60 | 6 | 11 |
| Ex. 162 | 1000 | 140 | 60 | 6 | 11 |
| Ex. 163 | 1000 | 160 | 61 | 5 | 11 |
| Ex. 164 | 1000 | 200 | 62 | 5 | 11 |
| Ex. 165 | 1000 | 300 | 62 | 5 | 10 |
| Ex. 166 | 1200 | 100 | 62 | 5 | 10 |
| Ex. 167 | 1200 | 140 | 62 | 5 | 10 |
| Ex. 168 | 1200 | 160 | 62 | 5 | 10 |
| Ex. 169 | 1200 | 200 | 62 | 5 | 10 |
| Ex. 170 | 1200 | 300 | 62 | 5 | 10 |
| Com. Ex. 46 | 500 | 100 | 51 | 12 | 16 |
| Com. Ex. 47 | 500 | 200 | 52 | 12 | 16 |
| Com. Ex. 48 | 700 | 100 | 54 | 8 | 14 |
| Com. Ex. 49 | 700 | 200 | 55 | 8 | 14 |
| Com. Ex. 50 | 910 | 80 | 54 | 8 | 14 |

EXAMPLE 171 to 187 and COMPARATIVE EXAMPLES 51 to 55

(Water Vapor Permeability: 740 g/m$^2$·24 h)

Body warmers were prepared and predetermined measurements were carried out in the same manner as Example 1 except that water vapor permeability of air permeable surfaces of inner bags was changed to 740 g/m$^2$·24 h. The results are summarized in Table 11.

TABLE 11

| No. | Iodine adsorption (mg/g) | Methylene blue decoloring power (mg/g) | Maximum Temp. (°C.) | Rise-time (min.) | Duration (hour) |
|---|---|---|---|---|---|
| Ex. 171 | 880 | 100 | 57 | 7 | 12 |
| Ex. 172 | 880 | 200 | 58 | 7 | 12 |
| Ex. 173 | 910 | 100 | 58 | 7 | 12 |
| Ex. 174 | 910 | 140 | 58 | 7 | 12 |
| Ex. 175 | 910 | 160 | 60 | 6 | 11 |
| Ex. 176 | 910 | 200 | 60 | 6 | 11 |
| Ex. 177 | 910 | 300 | 61 | 6 | 11 |
| Ex. 178 | 1000 | 100 | 61 | 5 | 11 |
| Ex. 179 | 1000 | 140 | 61 | 5 | 11 |
| Ex. 180 | 1000 | 160 | 62 | 5 | 11 |
| Ex. 181 | 1000 | 200 | 62 | 5 | 11 |
| Ex. 182 | 1000 | 300 | 62 | 4 | 11 |
| Ex. 183 | 1200 | 100 | 62 | 4 | 11 |
| Ex. 184 | 1200 | 140 | 63 | 4 | 10 |
| Ex. 185 | 1200 | 160 | 63 | 4 | 10 |
| Ex. 186 | 1200 | 200 | 63 | 4 | 10 |
| Ex. 187 | 1200 | 300 | 63 | 4 | 10 |
| Com. Ex. 51 | 500 | 100 | 51 | 12 | 15 |
| Com. Ex. 52 | 500 | 200 | 52 | 12 | 15 |
| Com. Ex. 53 | 700 | 100 | 54 | 8 | 14 |
| Com. Ex. 54 | 700 | 200 | 55 | 8 | 14 |
| Com. Ex. 55 | 910 | 80 | 54 | 8 | 14 |

EXAMPLE 188 to 204 and COMPARATIVE EXAMPLES 56 to 60

(Water Vapor Permeability: 1000 g/m$^2$·24 h)

Body warmers were prepared and predetermined measurements were carried out in the same manner as Example 1 except that water vapor permeability of air permeable surfaces of inner bags was changed to 1000 g/m$^2$·24 h. The results are summarized in Table 12.

TABLE 12

| No. | Iodine adsorption (mg/g) | Methylene blue decoloring power (mg/g) | Maximum Temp. (°C.) | Rise-time (min.) | Duration (hour) |
|---|---|---|---|---|---|
| Ex. 188 | 880 | 100 | 57 | 6 | 12 |
| Ex. 189 | 880 | 200 | 58 | 6 | 12 |
| Ex. 190 | 910 | 100 | 59 | 6 | 11 |
| Ex. 191 | 910 | 140 | 60 | 6 | 11 |
| Ex. 192 | 910 | 160 | 62 | 5 | 11 |
| Ex. 193 | 910 | 200 | 62 | 5 | 11 |
| Ex. 194 | 910 | 300 | 62 | 5 | 11 |
| Ex. 195 | 1000 | 100 | 63 | 4 | 10 |
| Ex. 196 | 1000 | 140 | 63 | 4 | 10 |
| Ex. 197 | 1000 | 160 | 63 | 4 | 10 |
| Ex. 198 | 1000 | 200 | 63 | 4 | 10 |
| Ex. 199 | 1000 | 300 | 63 | 4 | 10 |
| Ex. 200 | 1200 | 100 | 63 | 4 | 10 |
| Ex. 201 | 1200 | 140 | 63 | 4 | 10 |
| Ex. 202 | 1200 | 160 | 64 | 4 | 9 |
| Ex. 203 | 1200 | 200 | 64 | 4 | 9 |
| Ex. 204 | 1200 | 300 | 64 | 4 | 9 |
| Com. Ex. 56 | 500 | 100 | 52 | 9 | 15 |
| Com. Ex. 57 | 500 | 200 | 53 | 9 | 14 |
| Com. Ex. 58 | 700 | 100 | 55 | 7 | 14 |
| Com. Ex. 59 | 700 | 200 | 56 | 7 | 14 |
| Com. Ex. 60 | 910 | 80 | 55 | 7 | 14 |

Samples were prepared and measurements were performed similarly in the case of water vapor permeability of 1450 g/m$^2$·24 h, however, the inner bags bulged due to gas generation and clogging thereof to make measurements based on JIS impossible.

Further, with respect to all Examples and Comparative Examples, the heat-generating agents agglomerated when the amount of silica gel was 0 or 0.5%, they more or less agglomerated when the amount of silica gel was 1%, 1.5% or 2%, and they did not agglomerate when the amount of silica gel was 2.5%, 3%, 3.5% or 4%.

Some body warmers were prepared using alumina instead of silica gel and similar experiments were carried out. The same effects were obtained in the case silica gel.

Moreover, some experiments were carried out in order to measure the amount of hydrogen gas generated under hermetically sealed condition (i.e. an inner bag containing a heat-generating agent therein is contained in an airtight outer bag). 36 g of heat-generating agent obtained by mixing 56 parts of reduced iron powder MR-2 (iron powder produced by Dowa Teppun Kogyo Kabushiki Kaisha), 27 parts of 10% brine, 9 parts of Hirukon S-1 (vermiculite produced by Hiruishi Kagaku Kogyo Kabushiki Kaisha), 3 parts of activated carbon, 3 parts of Silica Gel HA 40 (silica gel produced by Fuji Shirishia Kagaku Kabushiki Kaisha) and 2 parts of KI Gel-201K (water-absorbing resin produced by Kuraray Co., Ltd.) was charged into an inner bag. The inner bag was contained in an aluminum bag and hermetically sealed. The outer bag containing inner bag was kept in a thermostat of 70° C. for 24 hours. The difference in volume of outer bag between after and before heating was measured. The number of samples tested was 5. The results are summarized in Table 13.

TABLE 13

| No. | Iodine adsorption (mg/g) | Methylene blue decoloring powder (mg/g) | Amount of gas generated (ml) | | | | | |
|---|---|---|---|---|---|---|---|---|
| | | | Sample A | Sample B | Sample C | Sample D | Sample E | Average |
| Ex. 205 | 1050 | 190 | 44 | 36 | 37 | 37 | 29 | 36.6 |
| Ex. 206 | 980 | 160 | 25 | 34 | 28 | 23 | 28 | 27.6 |
| Ex. 206 | 880 | 110 | 27 | 19 | 24 | 27 | 20 | 23.4 |
| Com. Ex. 61 | 700 | 100 | 80 | 69 | 64 | 70 | 71 | 70.8 |
| Com. Ex. 62 | 500 | 100 | 73 | 64 | 66 | 65 | 58 | 65.2 |

As is clear from Tables 1 to 12, the rise-time of disposable body warmers of the present invention is short, and duration can be maintained for a long period. Further, it is understood that agglomeration of body warmers after use can be prevented by adding 2 to 6% of silica gel to heat-generating agent.

Further, as is clear from Table 13, a heat-generating agent in the present invention which includes activated carbon of high quality generates less gas than in the case of conventional heat-generating agent.

As explained above, according to the present invention, there can be obtained a disposable body warmer having short rise-time. Further, by adding 2 to 6% of silica gel and/or alumina to the heat-generating agent, the bulging of the bag and agglomeration of the heat-generating agent after use can be prevented.

As stated above, a disposable body warmer of the present invention is useful as a portable body warmer because it raises its temperature in a short time, maintains a suitable duration and avoids loss of inner bags manufactured.

What is claimed is:

1. A disposable body warmer comprising a heat-generating agent which oxidizes and generates heat by the presence of air, a flat bag having two opposed surfaces containing the heat-generating agent and an airtight bag containing the flat bag, wherein at least one surface of the flat bag is made air permeable so that pressure in the flat bag is reduced by an exothermic reaction of the heat-generating agent, a self-adhesive layer is provided on either surface of the flat bag, and the heat-generating agent contains high performance activated carbon having an iodine adsorption of 800 to 1200 mg/g and a methylene blue decoloring power of 100 to 300 mg/g.

2. The disposable body warmer of claim 1, wherein water vapor permeability of the air permeable surface of the flat bag is from 340 to 1000 g/m$^2$·24 h.

3. The disposable body warmer of claim 1, wherein water vapor permeability of the air permeable surface of the flat bag is from 350 to 700 g/m$^2$·24 h.

4. The disposable body warmer of any one of claims 1 to 3, wherein the heat-generating agent contains 2 to 6% by weight of at least one of silica gel and alumina.

* * * * *